(12) United States Patent
Nycz et al.

(10) Patent No.: US 8,979,849 B2
(45) Date of Patent: Mar. 17, 2015

(54) OSTEOCHONDRAL IMPLANT FIXATION PROCEDURE AND BONE DILATOR USED IN SAME

(75) Inventors: Jeffrey H. Nycz, Warsaw, IN (US); Daniel Andrew Shimko, Germantown, TN (US); Jeetendra Subhash Bharadwaj, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 551 days.

(21) Appl. No.: 12/828,536

(22) Filed: Jul. 1, 2010

(65) Prior Publication Data

US 2010/0268261 A1 Oct. 21, 2010

Related U.S. Application Data

(62) Division of application No. 11/340,024, filed on Jan. 26, 2006, now Pat. No. 7,776,043.

(51) Int. Cl.
*A61F 2/46* (2006.01)
*A61F 2/30* (2006.01)

(52) U.S. Cl.
CPC ..... *A61F 2/4618* (2013.01); *A61F 2002/30217* (2013.01); *A61F 2002/30574* (2013.01); *A61F 2002/30594* (2013.01); *A61F 2230/0067* (2013.01)
USPC .............................. 606/86 R; 606/99; 606/105

(58) Field of Classification Search
CPC .................................................... A61F 2/4601
USPC ................... 623/1.3; 600/201, 206, 208, 219; 606/86 R, 99, 105
See application file for complete search history.

(56) References Cited

U.S. PATENT DOCUMENTS

| | | | |
|---|---|---|---|
| 4,936,851 A | 6/1990 | Fox et al. | |
| 5,405,388 A | 4/1995 | Fox | |
| 5,569,205 A | 10/1996 | Hart et al. | |
| 5,836,913 A | 11/1998 | Orth et al. | |
| 5,842,477 A | 12/1998 | Naughton et al. | |
| 5,919,196 A | 7/1999 | Bobic et al. | |
| 5,990,382 A | 11/1999 | Fox | |
| 6,436,119 B1* | 8/2002 | Erb et al. | 606/198 |
| 6,589,225 B2 | 7/2003 | Orth et al. | |
| 6,591,581 B2 | 7/2003 | Schmieding | |
| 6,626,945 B2 | 9/2003 | Simon et al. | |
| 6,851,430 B2 | 2/2005 | Tsou | |
| 7,264,634 B2 | 9/2007 | Schmieding | |
| 7,591,820 B2 | 9/2009 | Schmieding et al. | |
| 7,722,614 B2 | 5/2010 | Shimko et al. | |
| 8,394,100 B2* | 3/2013 | Lyons | 606/84 |
| 2004/0117019 A1* | 6/2004 | Trieu et al. | 623/17.11 |
| 2006/0052787 A1 | 3/2006 | Re et al. | |
| 2006/0178748 A1* | 8/2006 | Dinger et al. | 623/18.11 |
| 2006/0235516 A1 | 10/2006 | Cavazzoni | |
| 2006/0247790 A1* | 11/2006 | McKay | 623/23.44 |
| 2007/0149982 A1 | 6/2007 | Lyons | |
| 2007/0172506 A1 | 7/2007 | Nycz et al. | |
| 2007/0173852 A1 | 7/2007 | Gil et al. | |

\* cited by examiner

*Primary Examiner* — Ellen C Hammond
(74) *Attorney, Agent, or Firm* — Sorell Lenna & Schmidt LLP

(57) ABSTRACT

A dilator for adapted to implant a graft in a bone. The dilator includes a hollow frusto conical configuration having a distal and proximal end, a continuous tapered outer surface extending from said distal end to said proximal end of said dilator, the continuous tapered outer surface configured to engage a bone in order to radially expand the bone outwardly as the dilator is advanced into an opening, one end of dilator having a cross-section less than the cross-section of the opening for insertion into the opening, and the other end of the dilator having a cross-section greater than the cross-section of the opening so that insertion of the body member in the opening expands the opening.

20 Claims, 2 Drawing Sheets

OSTEOCHONDRAL IMPLANT FIXATION PROCEDURE AND BONE DILATOR USED IN SAME

CROSS-REFERENCE TO RELATED APPLICATIONS

This application is a divisional of U.S. application Ser. No. 11/340,024, filed Jan. 26, 2006, now U.S. Pat. No. 7,776,043, the entirety of which is incorporated by reference.

BACKGROUND

This invention relates to an improved osteochondral implant fixation method and, more particularly, to such a method in which a recipient hole is prepared for receiving a graft.

In the human body, the knee consists of three bones—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" and "OATS", has been used to repair articular cartilages. This procedure involves removing injured tissue from the articular opening and drilling cylindrical holes in the base of the opening and underlying bone. Cylindrical plugs, consisting of healthy cartilage overlying bone, are obtained from another area of the patient, typically from a lower weight-bearing region of the joint under repair, or from a donor patient, and are implanted in the holes. However, in these cases, if the hole is too large, the graft can rotate in the hole and become loose, which will prevent integration with the surrounding tissues. If the hole is too small, significant cellular damage can occur to the graft during the implantation.

An embodiment of the present invention involves a graft implantation technique that overcomes the above problems.

DETAILED DESCRIPTION

Figure 1:
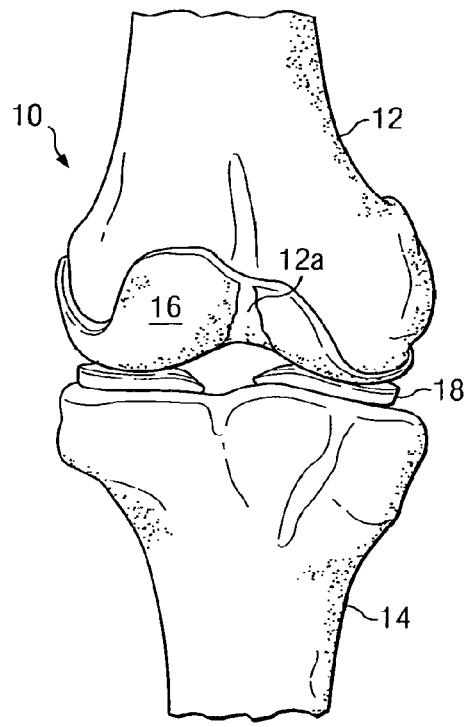
FIG. 1 is a elevational view of a human knee with certain parts removed in the interest of clarity.

Referring to FIG. 1 of the drawing, the reference numeral 10 refers, in general, to a knee area of a human including a femur 12 and a tibia 14 whose respective chondral areas are in close proximity to form a joint. A cartilage 16 extends over a portion of the chondral area of the femur 12, and a meniscus 18 overlies a portion of the chondral area of the tibia 14 and extends between the tibia and the cartilage. The patella, as well as the related tendons and quadriceps that also form part of the knee, are not shown in the interest of clarity.

It will be assumed that a portion of the cartilage 16 in the chrondral area of the femur 12 has been damaged and removed by the surgeon, or has worn away, exposing a damaged area, or defect 12a, and that it is desired to implant a graft in the defect.

Figure 2:
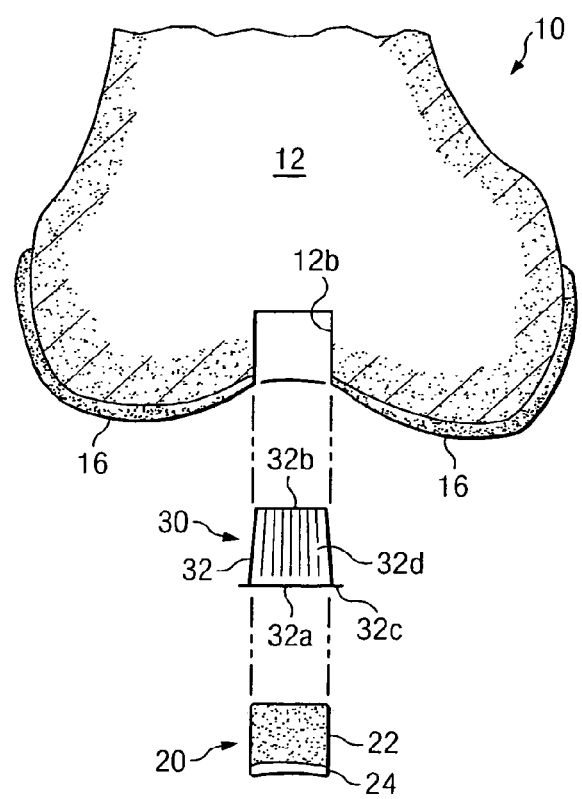
FIG. 2 is an exploded view, illustrating the grafting technique according to an embodiment of the invention.

Referring to FIG. 2, a graft 20 is obtained from one of several sources. For example, it could be harvested from another area of the patient/recipient, such as a undamaged non-load bearing area of the femur or tibia that has cartilage extending over a portion of its chondral area. Alternately it could be obtained from a cadaveric donor, a living donor, or it could be of xenogenic origin, or of an artificial substitute material.

The graft 20 has a circular cross-section and includes a bony portion 22 and a cartilage portion 24 overlying the bony portion 22.

A recipient opening 12b is formed in the defect 12a that is shaped the same as the graft 20, but has a diameter that is slightly smaller than that of the graft. An exemplary technique for forming the opening 12b would be to drill a hole in the femur 12 to a depth substantially corresponding to the height of the graft 20.

A dilator 30 is provided that consists of a hollow body member 32 having a wall that tapers radially inwardly from one end 32a of the body member to its other end 32b to form a hollow frusto-cone. An annular lip 32c extends outwardly from the end 32a, and a series of spaced, longitudinal slits, or slots, 32d are formed through the wall forming the body member 32 to add flexibility to the wall, for reasons to be described.

The diameter of the end 32b of the body member 32 is less than the diameter of the opening 12b so that the end can be inserted in the opening. The diameter of the end 32a is greater than that of the opening 12b to cause expansion of the opening in a manner to be described. The diameter of the end 32a of the body member 32 is greater than the diameter of the graft 20 so as to receive the graft, and the diameter of the end 32b is less than that of the graft so that, when the graft is inserted in the body member, the body member will expand, also in a manner to be described.

Figure 3:
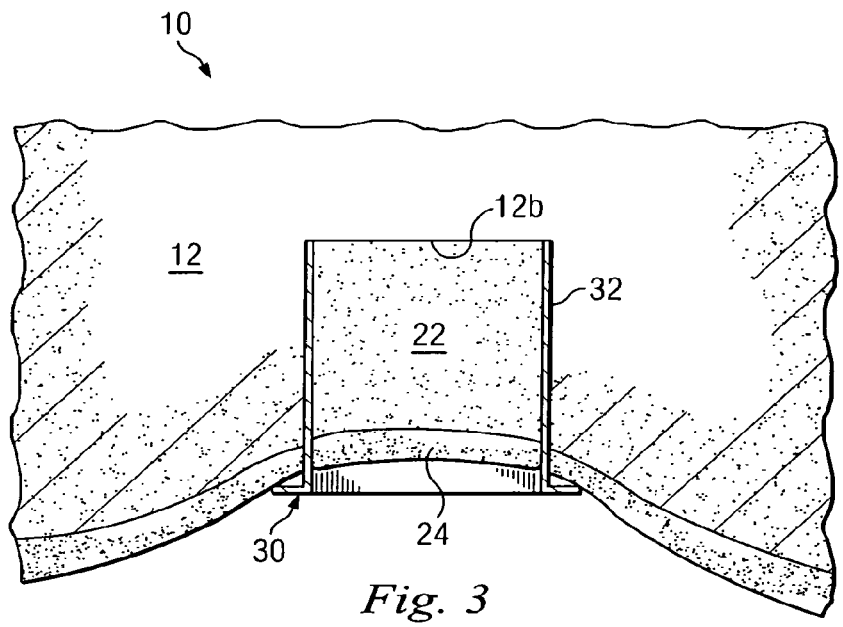
FIGS. 3 and 4 are enlarged sectional views depicting steps in the grafting technique.

Referring to FIGS. 2 and 3, after the opening 12b is formed during the surgical procedure, the end 32b of the dilator 30 is initially inserted into the opening 12b either by hand or using any suitable instrument. Then, as the dilator 30 is pushed, or forced, in an axial direction into the opening 12b, its tapered outer surface engages the inner wall of the opening and exerts outwardly-directed radial forces against the latter wall. Sufficient force is exerted to drive the dilator 30 axially into the opening until the end 32b engages the bottom of the opening 12b and the lip 32c engages the chrondral surface of the femur 12 surrounding the opening 12b. Due to the fact that the diameter of the end 32a, as well as a portion of the tapered body member 32 adjacent the latter end (the lower portion of the dilator 32 as viewed in FIG. 2), is greater than that of the opening 12b, the opening, and, more particularly, the tissue and bony portion of the femur 12 defining the opening, is expanded radially outwardly as the dilator moves to its completely embedded position in the opening shown in FIG. 3.

The graft 20 is then inserted into the opening 12b either by hand or using any suitable instrument. The graft 20 is then pushed, or forced, in an axial direction into the body member 32 with the outer surface of the graft engaging the inner surface of the tapered inner wall of the body member 32, to exert outwardly-directed radial forces against the latter wall. Due to the fact that the diameter of the graft 20 is greater than the upper portion of the tapered body member 32 as viewed in FIGS. 2 and 3, the body member is expanded radially outwardly, aided by the slots 32d, as the graft moves axially in the body member. This expansion of the body member 32 causes corresponding additional expansion of the opening 12b. This movement continues until the leading end of the graft 20 engages the bottom of the opening 12b, as shown in FIG. 3. In the position of FIG. 3, the dilator 30 extends in the opening 12b in a snug fit and the graft 20 extends in the dilator in a snug fit.

Figure 4:
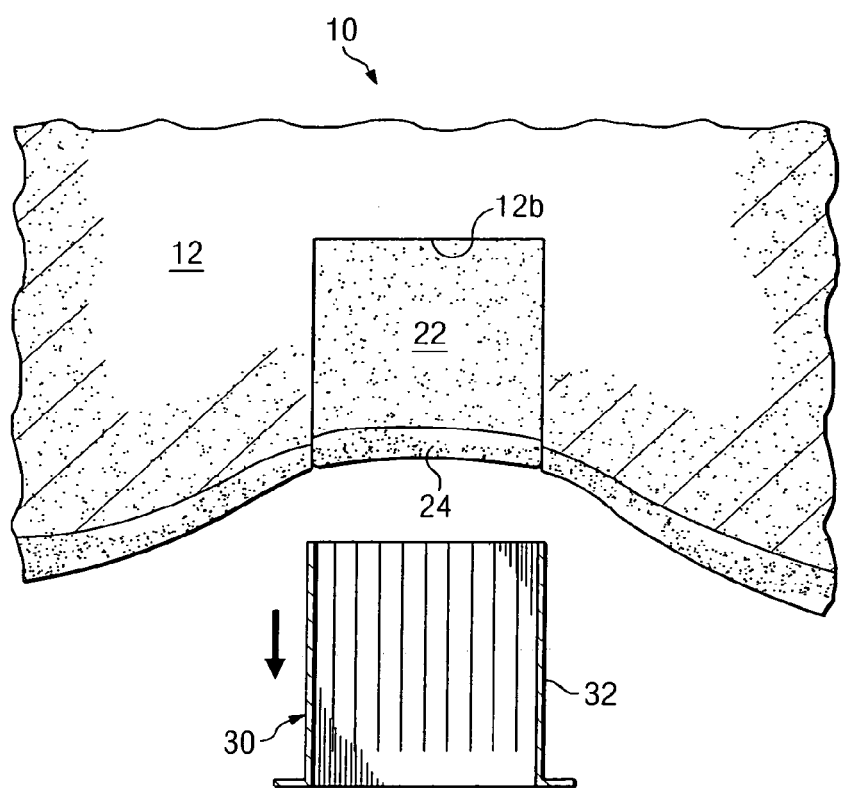

With reference to FIG. 4, the dilator 30 is manually extracted from the opening in the direction shown by the arrow, thus forming an interface between the graft 20 and the wall of the femur 12 defining the opening 12b. The expanded bony portion and tissue of the femur 12 surrounding the graft 20 will then collapse around the graft, thus producing compression that retains the graft in the opening 12b. This prevents any relative movement between the graft 20 and the opening 12b and promotes integration of the graft with the surrounding bone and tissue of the femur 12.

Variations

1. The dimensions of the graft, the dilator and/or the opening, can vary within the scope of the invention.

2. The relative dimensions between the graft, the dilator and/or the opening, can vary within the scope of the invention.

3. The shape of the graft, the dilator, and or the opening can vary within the scope of the invention. For example, the cross-section of the graft, the dilator, and the opening can be of a polygonal shape as disclosed in copending U.S. patent application Ser. No. 11/120,136, filed Apr. 30, 2005, the disclosure of which is hereby incorporated by reference.

4. The procedure and dilator discussed above are equally applicable to any animal species in addition to humans.

5. The graft can be harvested from the patient or another human, or can be a xenogenic source, or can be a substitute material.

6. The spatial references mentioned above, such as "upper", "lower", "under", "over", "between", "outer", "inner" and "surrounding" are for the purpose of illustration only and do not limit the specific orientation or location of the components described above.

Those skilled in the art will readily appreciate that many other variations and modifications of the embodiments described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A system comprising:
a bone graft; and
a dilator adapted for implanting the bone graft in an opening having an outer surface, side walls and a bottom in a bone of a patient, the dilator comprising:
a body member having a hollow frusto conical configuration having a distal and proximal end, and the frusto conical configuration including a plurality of circumferentially disposed slots having a continuous tapered outer surface and a uniform length extending from said distal end to said proximal end, wherein the distal end is configured to engage the bottom of the opening and the tapered outer surface is configured to engage the side walls of the opening;
an annular lip extending outwardly from the proximal end, wherein the lip is configured to engage the outer surface of the opening;
said continuous tapered outer surface configured to engage the bone in order to radially expand the bone outwardly as the dilator is advanced into the opening such that when the body member is removed, the bone contracts around the bone graft;
the distal end of the body member having a cross-section less than the a cross-section of the opening and adapted for insertion into the opening;
the proximal end of the body member having a cross-section greater than the a cross-section of the opening so that insertion of the body member in the opening expands the opening,
the cross-section of the proximal end of the body member is greater than the a cross-section of the bone graft and adapted to receive the bone graft, and
the cross-section of the distal end of the body member is less than that of the bone graft such that the insertion of the bone graft into the dilator expands the body member radially outwardly to further expand the opening and permit removal of the dilator from the opening leaving the bone graft therein.

2. The system of claim 1, wherein the slots promote the expansion.

3. The system of claim 1, wherein the slots are configured to expand as the bone graft moves into the body member, the dilator has a circular cross-section and wherein the expansion is in the radial direction.

4. The system of claim 1, wherein the slots are configured to apply a radial force to the sidewalls of the opening.

5. The system of claim 1, wherein the body member and the annular lip are monolithically formed such that the dilator is one piece.

6. The system of claim 1, wherein an interface between the lip and the proximal end has a maximum diameter that is greater than that of the distal end.

7. The system of claim 1, wherein the annular lip has a maximum diameter that is greater than that of the body member.

8. The system of claim 1, wherein:
the body member extends along a longitudinal axis between the proximal and distal ends; and
the body member comprises an inner surface defining a passageway and one of the proximal end and the distal end includes an aperture extending parallel to the longitudinal axis that is in communication with the passageway and configured for disposal of the bone graft.

9. The system of claim 8, wherein the body member is movable between a first configuration in which the bone graft is spaced apart from the passageway and the passageway is tapered along an entire length of the passageway and a second configuration in which the bone graft is disposed in the passageway and the passageway has a uniform diameter along the entire length of the passageway.

10. The system of claim 1, wherein the bone graft comprises a cartilage portion overlying a bony portion of the bone graft, the bone graft being configured to integrate with the bone.

11. A system comprising:
a bone graft; and
a dilator having a hollow frusto conical configuration having a side wall, the side wall including a uniform length and a plurality of circumferentially disposed slots extending between a distal end and an opposite proximal end, the proximal end comprising an annular lip extending outwardly from the side wall, the side wall being tapered continuously from an interface between the lip and the side wall to a distal end surface of the distal end, the dilator comprising an inner surface defining a passageway,
wherein the dilator is movable between a first configuration in which the bone graft is spaced apart from the passageway and the passageway is tapered along an entire length of the passageway and a second configuration in which the bone graft is disposed in the passageway and the passageway has a uniform diameter along the entire length of the passageway.

12. The system of claim 11, wherein:
the distal end defines a first end surface and the annular lip defines a second end surface opposite the first end surface, a distance between the first and second end surfaces defining a maximum height of the dilator,
the dilator extends along a longitudinal axis between the proximal and distal ends, the annular lip projecting outwardly from the side wall and extending perpendicular to the longitudinal axis, and
the annular lip has a maximum diameter that is greater than that of the side wall.

13. The system of claim 11, wherein the proximal end comprises an aperture having a cross-section that is greater than a cross-section of the bone graft, the aperture being adapted is to receive the bone graft.

14. The system of claim 13, wherein the distal end has a cross-section that is less than a cross-section of the bone graft such that insertion of the bone graft into the passageway expands the dilator radially outwardly.

15. The system of claim 11, wherein:
the dilator extends along a longitudinal axis between the proximal and distal ends; and
the side wall comprises a plurality of spaced apart slots extending parallel to the longitudinal axis.

16. The system of claim 11, wherein the bone graft comprises a cartilage portion overlying a bony portion of the bone graft.

17. The system of claim 11, wherein the bone graft is configured to replace a portion of a bone of a patient.

18. The system of claim 11, wherein:
the bone graft has a maximum height that is less than a distance between the annular lip and the distal end; and
the bone graft is positioned entirely within the dilator between the annular lip and the distal end.

19. The system of claim 11, wherein the dilator extends along a longitudinal axis between the distal end and the proximal end and the annular lip extends perpendicular to the longitudinal axis.

20. A system comprising:
a bone graft comprising a cartilage portion overlying a bony portion of the bone graft, the bone graft being configured to replace a portion of a bone of a patient and integrate with the bone; and
a dilator adapted for implanting the bone graft in an opening in the bone, the dilator comprising a hollow frusto conical configuration having a distal end comprising a first end surface and a proximal end opposite the distal end, the frusto conical configuration including a uniform length and a plurality of circumferentially disposed slots extending between the proximal end and the distal end, the dilator comprising an annular lip extending outwardly from the proximal end, the annular lip defining a second end surface opposite the first end surface, a distance between the end surfaces defining a maximum height of the dilator,
wherein the bone graft has a maximum height that is less than the maximum height of the dilator such that the bone graft is positioned entirely within the dilator between the annular lip and the distal end, and
wherein an outer surface of the dilator is tapered and comprises a plurality of slots extending therethrough configured to promote radial expansion of the dilator as the bone graft is positioned within the dilator.

* * * * *